(12) United States Patent
Strassner et al.

(10) Patent No.: US 11,653,925 B2
(45) Date of Patent: May 23, 2023

(54) TISSUE RELAXATION MONITORING FOR OPTIMIZED TISSUE STAPLING

(71) Applicant: Covidien LP, Mansfield, MA (US)

(72) Inventors: Haley Strassner, Hamden, CT (US); David E. Valentine, Hamden, CT (US); Alexander J. Hart, Tolland, CT (US); Stephen R. Casey, Wallingford, CT (US); Sonya A. Bader, Plainville, MA (US); James P. Delbo, North Haven, CT (US); Charles R. Kollar, Washington, DC (US); Drew R. Seils, Guilford, CT (US); Steven H. Joyce, Durham, CT (US)

(73) Assignee: COVIDIEN LP, Mansfield, MA (US)

( * ) Notice: Subject to any disclaimer, the term of this patent is extended or adjusted under 35 U.S.C. 154(b) by 71 days.

(21) Appl. No.: 17/313,833

(22) Filed: May 6, 2021

(65) Prior Publication Data

US 2021/0361288 A1    Nov. 25, 2021

Related U.S. Application Data

(60) Provisional application No. 63/028,136, filed on May 21, 2020.

(51) Int. Cl.
*A61B 17/115* (2006.01)
*A61B 34/00* (2016.01)
(Continued)

(52) U.S. Cl.
CPC ........... *A61B 17/1155* (2013.01); *A61B 34/76* (2016.02); *A61B 2017/00022* (2013.01);
(Continued)

(58) Field of Classification Search
CPC ............... A61B 17/1155; A61B 34/76; A61B 2017/00022; A61B 2017/00119;
(Continued)

(56) References Cited

U.S. PATENT DOCUMENTS

| 3,193,165 A | 7/1965 | Akhalaya et al. |
| 3,388,847 A | 6/1968 | Kasulin et al. |

(Continued)

FOREIGN PATENT DOCUMENTS

| CA | 908529 A | 8/1972 |
| CA | 2805365 A1 | 8/2013 |

(Continued)

OTHER PUBLICATIONS

European Search Report dated Oct. 21, 2021, corresponding to counterpart European Application No. 21175125.0; 7 pages.

(Continued)

*Primary Examiner* — Andrew M Tecco
*Assistant Examiner* — Nicholas E Igbokwe
(74) *Attorney, Agent, or Firm* — Carter, DeLuca & Farrell, LLP

(57) ABSTRACT

A circular stapling device includes a handle assembly including a processor, an adapter assembly including a trocar assembly and a strain gauge assembly, a reload assembly operably secured to the adapter assembly, the reload assembly including a staple cartridge, and an anvil assembly releasably secured to the trocar assembly and moveably positioned relative to the staple cartridge between a spaced position and a clamped position. The processor includes software for determining when tissue clamped between the staple cartridge and the anvil assembly has achieved a predetermined tissue relaxation percent. A method of optimizing tissue relaxation during a stapling procedure includes clamping tissue between an anvil assem- (Continued)

bly and a reload assembly, calculating a tissue relaxation percent of the clamped tissue, and initiating a stapling sequence when the tissue relaxation percent equals or is less than a predetermined tissue relaxation percent.

19 Claims, 6 Drawing Sheets

(51) Int. Cl.
  *A61B 17/00* (2006.01)
  *A61B 17/072* (2006.01)
(52) U.S. Cl.
  CPC ............... *A61B 2017/00119* (2013.01); *A61B 2017/07257* (2013.01); *A61B 2017/07271* (2013.01); *A61B 2017/07285* (2013.01); *A61B 2562/0261* (2013.01)
(58) Field of Classification Search
  CPC ........... A61B 2017/07257; A61B 2017/07271; A61B 2017/07285; A61B 2562/0261
  See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |

(56) References Cited

U.S. PATENT DOCUMENTS

| | | |
|---|---|---|
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |

(56) References Cited

U.S. PATENT DOCUMENTS

| | | |
|---|---|---|
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |

(56) References Cited

U.S. PATENT DOCUMENTS

| | | |
|---|---|---|
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |

(56) References Cited

U.S. PATENT DOCUMENTS

| | | |
|---|---|---|
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Dingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2016/0007999 A1* | 1/2016 | Latimer ............. A61B 17/1155 227/177.1 |
| 2018/0067004 A1* | 3/2018 | Sgroi, Jr. .................. G01L 1/26 |
| 2018/0353186 A1* | 12/2018 | Mozdzierz .......... A61B 17/072 |
| 2018/0360460 A1* | 12/2018 | Mozdzierz .......... A61B 17/3476 |
| 2019/0125361 A1 | 5/2019 | Shelton, IV et al. |
| 2019/0174636 A1* | 6/2019 | Sgroi, Jr. ........... A61B 17/1155 |
| 2019/0200981 A1* | 7/2019 | Harris .................... G16H 10/60 |
| 2019/0201042 A1* | 7/2019 | Nott ................... A61B 18/1233 |
| 2019/0274716 A1* | 9/2019 | Nott .................... A61B 17/295 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3412225 A1 | 12/2018 |
| EP | 3545862 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2008107918 A1 | 9/2008 |

OTHER PUBLICATIONS

Extended European Search Report from Appl. No. 14181908.6 dated May 26, 2015.

European Examination Report from Appl. No. 14181908.6 dated May 3, 2016.

\* cited by examiner

TISSUE RELAXATION MONITORING FOR OPTIMIZED TISSUE STAPLING

CROSS REFERENCE TO RELATED APPLICATION

This application claims the benefit of the filing date of provisional U.S. Application No. 63/028,136, filed on May 21, 2020.

FIELD

This disclosure is generally related to powered surgical stapling devices and, more particularly, to powered surgical stapling devices that include software that utilizes strain measurements to optimize stapling and/or cutting of tissue.

BACKGROUND

Powered surgical stapling devices include a handle assembly, an adapter assembly including a proximal portion supported on the handle assembly, and a tool assembly supported on the distal portion of the adapter assembly. The tool assembly often includes a reload assembly and an anvil assembly moveably positioned relative to the reload assembly to clamp tissue therebetween. The stapling device may also include a strain gauge for measuring characteristics of tissue being clamped and/or stapled, e.g., tissue thickness, tissue compression, etc., and/or parameters related to staple formation or tissue cutting, e.g., cutting force, firing force, etc. Typically, a strain gauge is supported within the adapter assembly and is formed from electronics that can be sterilized or reprocessed to facilitate reuse of the adapter assembly. Such electronics are costly.

During a stapling procedure, when clamping tissue many surgeons wait a specified period of time, e.g., fifteen seconds or more, after achieving a predetermined tissue gap between the anvil assembly and the reload assembly. This waiting period provides the clamped tissue with time to relax, e.g., allows fluid to travel out of the clamped tissue into surrounding tissue, and is intended to encourage a less traumatic staple firing. Waiting longer than is necessary for the clamped tissue to achieve an optimum relaxation extends the time of surgery. Conversely, not waiting a sufficient period of time for the tissue to relax can unnecessarily damage the stapled tissue and/or result in staple malformation.

Therefore, it would be beneficial to have a device for and method for monitoring tissue relaxation and indicating when optimum tissue relaxation is achieved.

SUMMARY

A circular stapling device includes a handle assembly including a processor, an adapter assembly operably secured to the handle assembly and including a trocar assembly and a strain gauge assembly, a reload assembly operably secured to the adapter assembly, the reload assembly including a staple cartridge, and an anvil assembly releasably secured to the trocar assembly and moveably positioned relative to the staple cartridge between a spaced position and a clamped position. The processor includes software for determining when tissue clamped between the staple cartridge and the anvil assembly has achieved a predetermined tissue relaxation percent, i.e., when the clamped tissue is determined to have stabilized.

In certain aspects of the disclosure, the predetermined tissue relaxation percent is between about 1% and about 0.5%. The strain gauge assembly may include a plurality of strain gauges. The software may be configured to activate an alert when the predetermined tissue relaxation percent is achieved. The software may alert the clinician with an audible, visual, and/or tactile feedback. The software may be configured to initiate a stapling sequence when the predetermined tissue relaxation percent is achieved. The software may be configured to activate an alert after the tissue is clamped for a predetermined time period. The predetermined time may be 15 seconds. The software may be configured to take samples of the clamping force at a predetermined sampling rate. The predetermined sampling rate may be 400 milliseconds.

A method of optimizing tissue relaxation during a stapling procedure includes clamping tissue between an anvil assembly and a reload assembly, calculating a tissue relaxation percent of the clamped tissue, and initiating a stapling sequence when the tissue relaxation percent equals or is less than a predetermined tissue relaxation percent.

In certain aspects of the disclosure, clamping the tissue includes moving the anvil assembly relative to the reload assembly until a predetermined gap is achieved between the anvil assembly and a staple cartridge of the reload assembly. Calculating the tissue relaxation percent may include using a 6-tap strain gauge history buffer. Initiating the stapling sequence may occur when the measured tissue relaxation percent is between about 0.05% and 1%. Initiating the stapling sequence may occur 15 seconds after clamping tissue is complete.

Aspects of the method may further include initiating a cutting sequence. The cutting sequence may be initiated at the completion of the stapling sequence. The cutting sequence may be initiated when the tissue relaxation percent equals or is less than a second predetermined tissue relaxation percent, or after a predetermined time period has elapsed, whichever occurs first. Initiating the cutting sequence may be automatic. Initiating the stapling sequence may occur when the tissue relaxation percent equals or is less than a predetermined tissue relaxation percent, or after predetermined time elapses, whichever occurs first.

BRIEF DESCRIPTION OF DRAWINGS

Various aspects and features of the disclosure are described with reference to the drawings wherein like numerals designate identical or corresponding elements in each of the several views, wherein.

DETAILED DESCRIPTION

Figure 1:
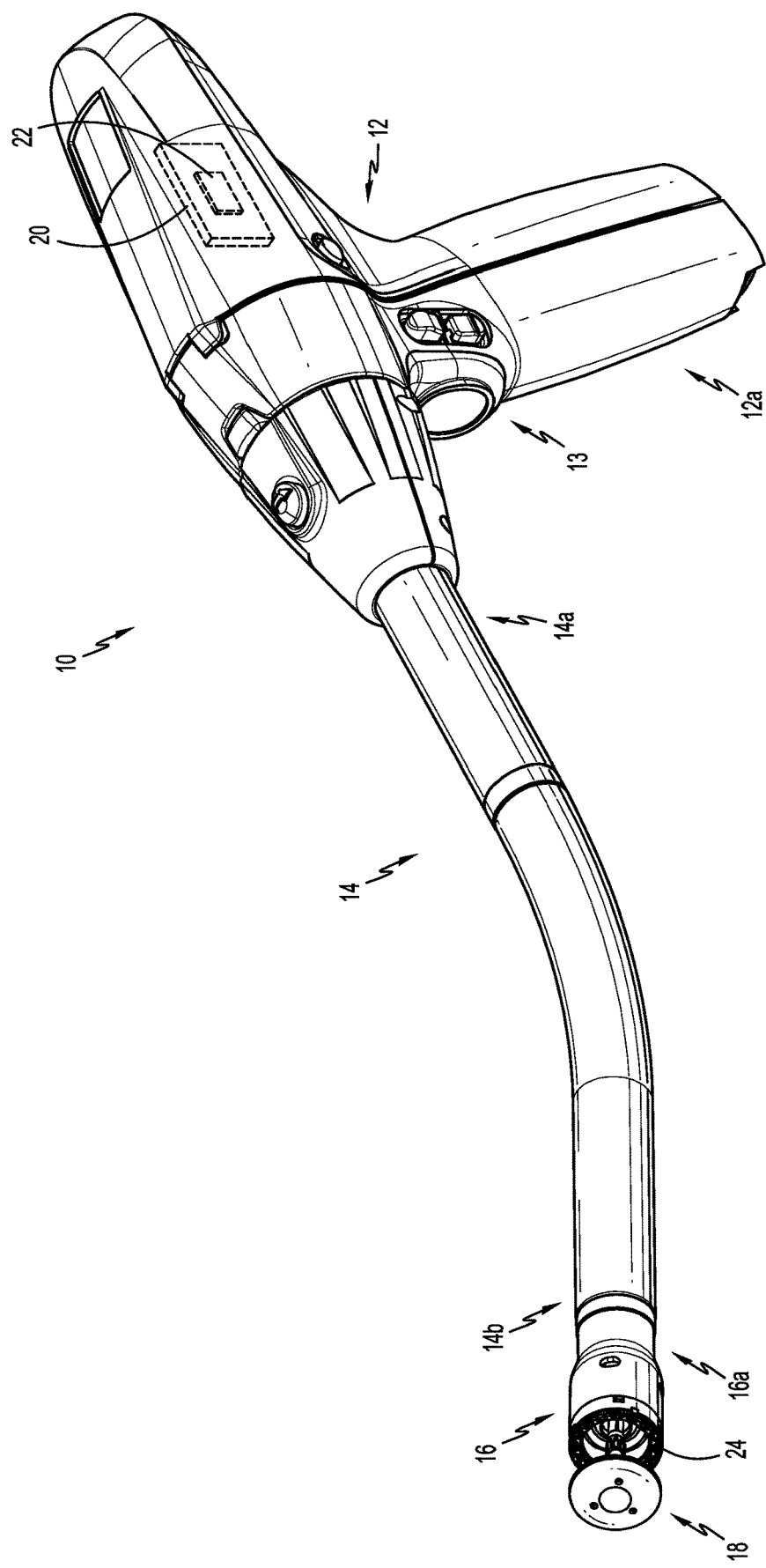
FIG. 1 is a side perspective view of a surgical stapling device including an adapter assembly having a strain gauge assembly according to aspects of the disclosure.

The devices and methods for optimizing tissue stapling are described in detail with reference to the drawings, in which like reference numerals designate identical or corresponding elements in each of the several views. As used herein the term "distal" refers to that portion of the component farther from the user, while the term "proximal" refers to that portion of the component closer to the user. In addition, the term "clinician" is used generally to refer to medical personnel including doctors, nurses, and support personnel. As used herein, the term "about" means that the numerical value is approximate and small variations would not significantly affect the practice of the disclosed aspects of the disclosure. Where a numerical limitation is used, unless indicated otherwise by the context, "about" means the numerical value can vary by ±10% of the stated value and remain within the scope of the disclosure.

The methods of optimizing tissue stapling described below utilize a strain gauge assembly of a circular stapling device to monitor strain gauge data, i.e., clamping force, during a stapling procedure. More particularly, and as will be described in further detail below, software in the stapling device uses strain gauge data to calculate a clamping force and measure the clamping force at a specified sampling rate. From this, a percent change in force between each data sample is calculated. The software then applies a filter by calculating an average percent change over a specified amount of percent change readings. When this average percent change calculated value is equal to or less than a specified tissue relaxation percent, the clinician is encouraged to initiate a firing sequence. If the average percent change value is not equal to or less than the tissue relaxation percent specified value before a predetermined period of time has elapsed, e.g., fifteen seconds (15 s), the clinician is encouraged to initiate the firing sequence after the predetermined period of time has passed.

FIG. 1 illustrates a circular stapling device 10 including a handle assembly 12, an elongate body or adapter assembly 14, a reload assembly 16 releasably supported on the adapter assembly 14, and an anvil assembly 18 releasably supported for movement in relation to the reload assembly 16 between an open position (FIG. 1) and a clamped position (not shown). Although the methods for optimizing tissue stapling will be described with reference to a circular stapling device, it is envisioned that the aspects of the disclosure may be modified for use in surgical stapling devices having alternative configurations.

The circular stapling device 10 is illustrated as an electrically powered stapling device including an electrically powered handle assembly 12 that may support one or more batteries (not shown). The adapter assembly 14 translates power from the handle assembly 12 to the reload and anvil assemblies 16, 18, respectively, to staple and cut tissue. Examples of electrically powered stapling devices can be found in U.S. Pat. Nos. 9,055,943 and 9,023,014, and U.S. Publication Nos. 2018/0125495 and 2017/0340351. Alternately, it is envisioned that aspects of the disclosure may be incorporated into a stapling device that is configured for use with a robotic system as disclosed in, e.g., U.S. Pat. No. 9,962,159, and does not include a handle assembly.

The handle assembly 12 of the circular stapling device 10 includes a stationary grip 12a that supports actuation buttons 13 for controlling operation of various functions of the circular stapling device 10, including, for example, approximation of the reload assembly 16 and anvil assembly 18, firing of staples from the reload assembly 16, and cutting or coring of tissue.

A processor 20 is disposed within the handle assembly 12 and includes or is operably connected to a memory chip 22. The memory chip 22 may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor 20 may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

The adapter assembly 14 includes a proximal portion 14a that can be releasably coupled to the handle assembly 12. The reload assembly 16 includes a proximal portion 16a that is releasably coupled to a distal portion 14b of the adapter assembly 14. A staple cartridge 24 is supported on a distal portion 16b of the reload assembly 16 and supports a plurality of surgical staples (not shown). A trocar assembly 26 is supported within the distal portion 14b of the adapter assembly 14 and extends through the reload assembly 16. The trocar assembly 26 includes a trocar member 28 for releasably securing and positioning the anvil assembly 18 relative to the reload assembly 16.

Figure 2:
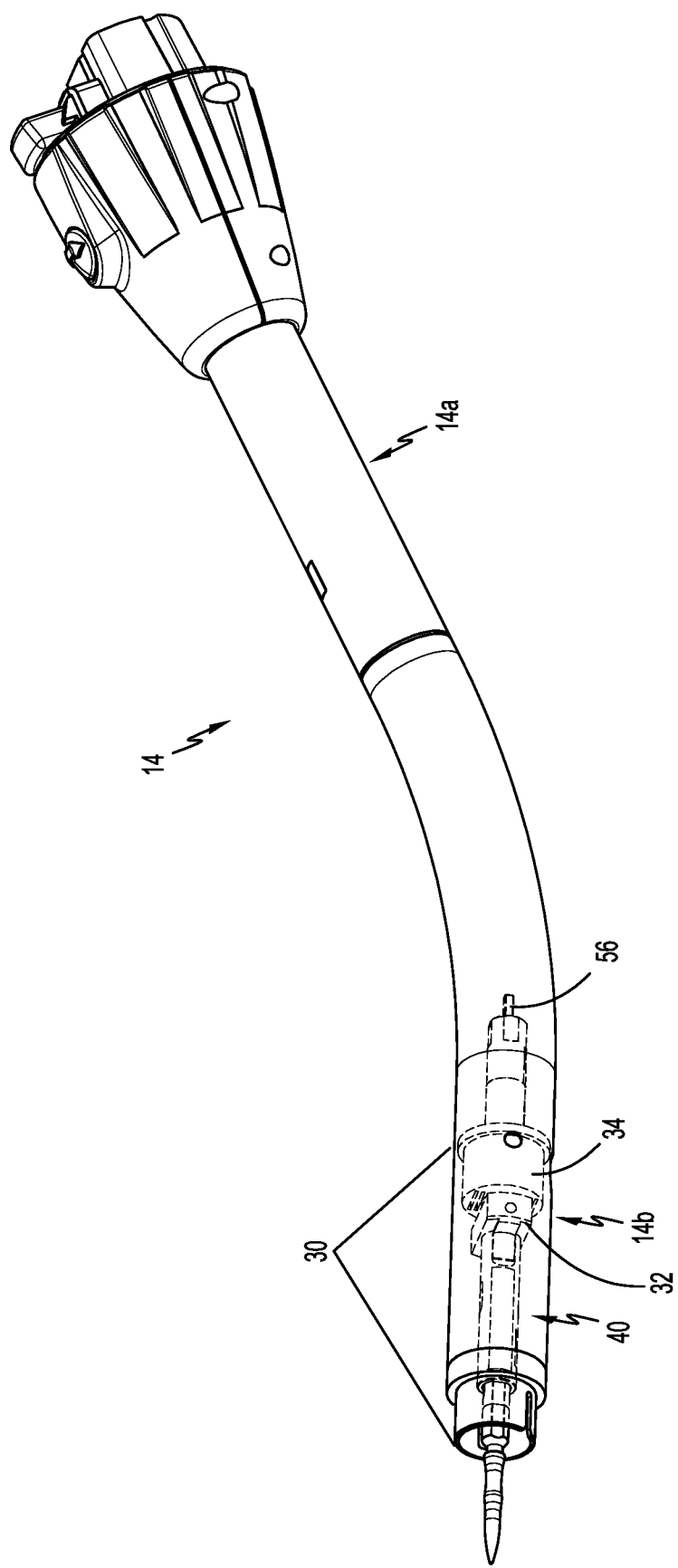
FIG. 2 is a side perspective view of the adapter assembly shown in FIG. 1 with a trocar assembly and strain gauge assembly shown phantom.
Figure 3:
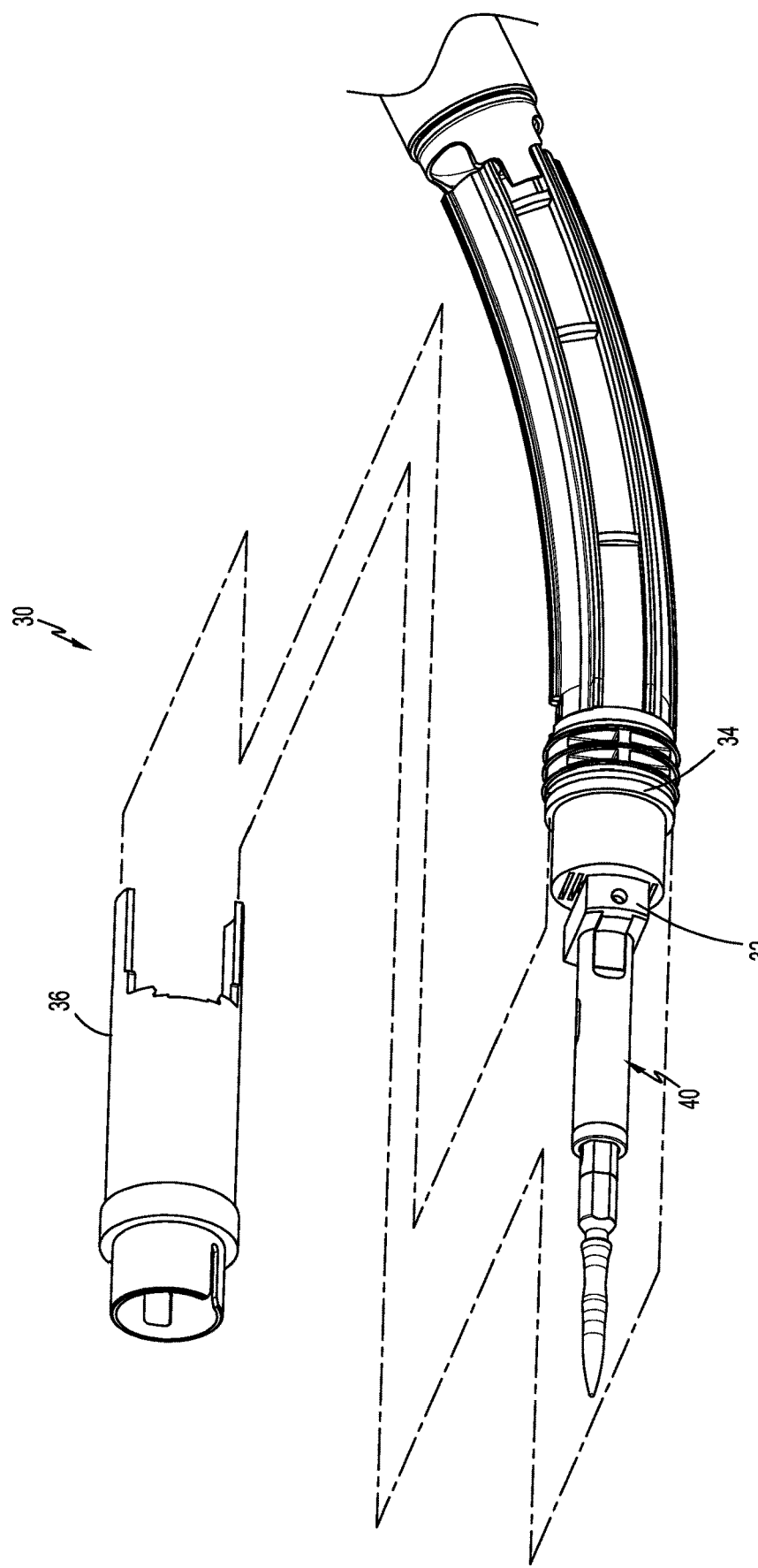
FIG. 3 is a side perspective view of a distal portion of the adapter assembly shown in FIG. 2, with an outer sleeve removed and a tension gauge support separated from the adapter assembly.
Figure 4:
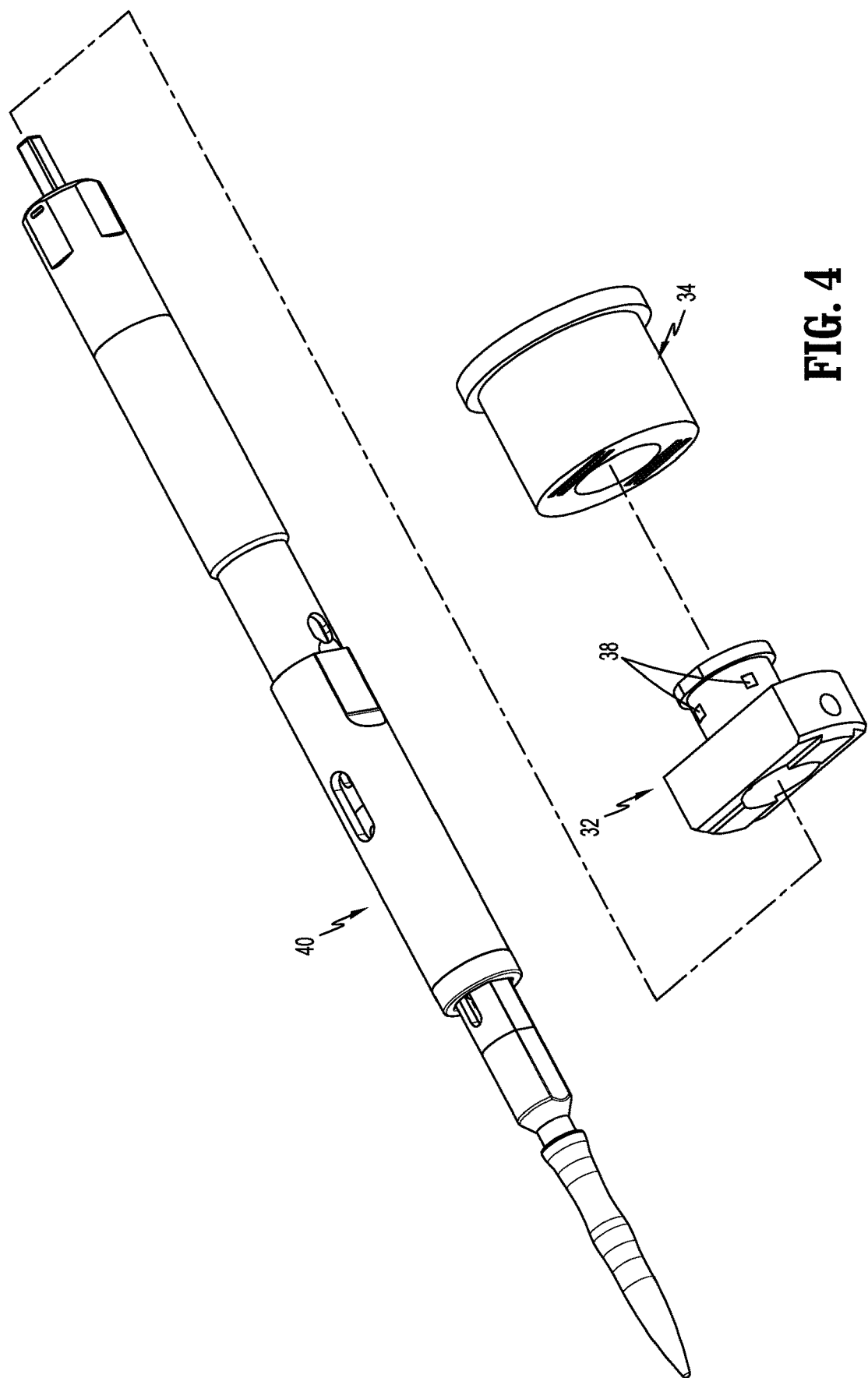
FIG. 4 is a side perspective view of the trocar assembly, and a tension gauge housing and tension gauge anchor of the strain gauge assembly, shown in FIG. 2.

FIGS. 2-4 illustrate a strain gauge assembly 30 supported within the distal portion 14b of the adapter assembly 14 (FIG. 2) and a trocar assembly 40 received through and supported by the strain gauge assembly 30. The strain gauge assembly 30 is positioned between the trocar assembly 40 and the reload assembly 16. With the strain gauge data provided by the strain gauge assembly 30, the clamping force between the staple cartridge 24 of the reload assembly 16 and the anvil assembly 18 can be calculated. The trocar assembly 40 releasably secures the anvil assembly 18 (FIG. 1) to the circular stapling device 10, and operates to advance and retract the anvil assembly 18 relative to the reload assembly 16. The software in the handle assembly 12 uses the strain gauge measurements to determine the clamping force over time. As will be described in further detail below, tissue relaxation occurs when the clamping force, i.e., the force on the tissue, stabilizes.

The strain gauge assembly 30 includes a tension gauge housing 32, a tension gauge anchor 34, and a tension gauge support 36 (FIG. 3). A plurality of strain gauges 38 are supported on an extension portion 32a (FIG. 4) of the tension gauge housing 32. For a detailed description of an exemplary strain gauge assembly, please refer to U.S. patent application Ser. No. 16/809,023, filed Mar. 4, 2020. Although shown as the strain gauge assembly 30, it is envisioned that the methods of the disclosure may be modified for use with any strain gauge assembly.

Figure 5:
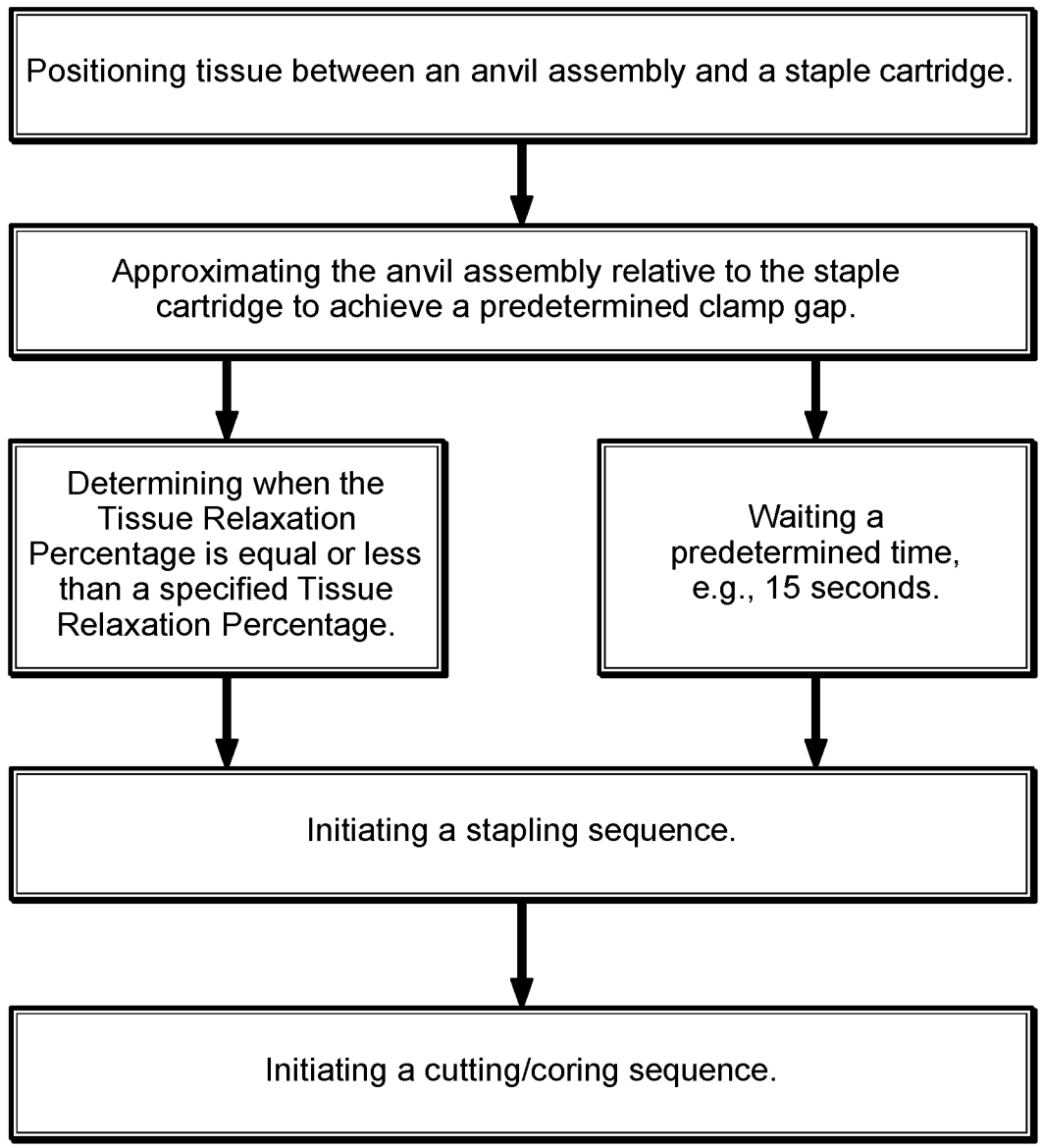
FIG. 5 is a flow diagram of a stapling sequence according to a method of the disclosure.

FIG. 5 illustrates a flow diagram of a stapling procedure for optimizing tissue stapling according to aspects of the disclosure. Initially, tissue to be stapled (not shown) is positioned between an anvil assembly, e.g., the anvil assembly 18 (FIG. 1), and a staple cartridge, e.g., staple cartridge 24 (FIG. 1) of a reload assembly, e.g., reload assembly 16 (FIG. 1). The anvil assembly is then approximated towards the reload assembly to clamp the tissue between the anvil assembly and the staple cartridge of the reload assembly. The anvil assembly is approximated towards the reload assembly until a predetermined clamp gap is achieved between the anvil assembly and the staple cartridge.

Strain gauge data provided by a strain gauge assembly, e.g., strain gauge assembly 30 (FIG. 2), is used to calculate a tissue relaxation percent, or more particularly, the percent change in the clamp force between two sample points. Tissue relaxation occurs when the compressed fluid within the clamped tissue has been able to flow into adjacent tissue, i.e., the clamping force stabilizes. Tissue relaxation is determined to have occurred when the tissue relaxation percent equals or is less than a predetermined tissue relaxation percent, typically 0.5-1.0%, or fifteen seconds have elapsed, whichever occurs first. In aspects of the disclosure, the software is configured to alert the clinician, through audio, visual, and/or tactile feedback, when optimum tissue relaxation has occurred and to initiate a stapling sequence. In certain aspects of the disclosure, the stapling procedure may be initiated at any time after the anvil assembly and staple cartridge achieve the clamp gap distance. It is also envisioned that the software may be programmed to automatically initiate the stapling sequence upon either the tissue relaxation percent being achieved, or 15 seconds elapsing.

Following the stapling sequence, a tissue cutting or coring sequence is initiated. The cutting sequence may be automatic, or may be manually initiated by the clinician. The cutting sequence may be initiated simultaneously with the stapling sequence, directly following the completion of the stapling sequence, or after a subsequent time period.

In certain aspects of the disclosure, tissue relaxation optimization similar to that of the tissue relaxation optimization described above can also be used prior to initiation of the cutting sequence to minimize tissue damage during cutting/coring of the stapled tissue. In this manner, subsequent to completion of the stapling sequence and prior to the initiation of the cutting sequence, the software in the handle assembly calculates a tissue relaxation percent from the strain gauge data provided by the strain gauge assembly. As with the stapling sequence, once the tissue relaxation percent is equal to or less than a predetermined tissue relaxation percent, or a predetermined time period has elapsed, whichever occurs first, the clinician is alerted that the cutting sequence may be initiated. It is envisioned that the cutting sequence may be initiated automatically.

In a further attempt to optimize tissue stapling, it is envisioned that the strain gauge assemblies may be used in combination with the software to monitor the clamping forces during tissue clamping. In the event the clamping forces exceed a predetermined threshold, the software can reduce the speed at which the tissue is being clamped, or stop clamping altogether until the clamping force has fallen below the threshold.

Figure 6:
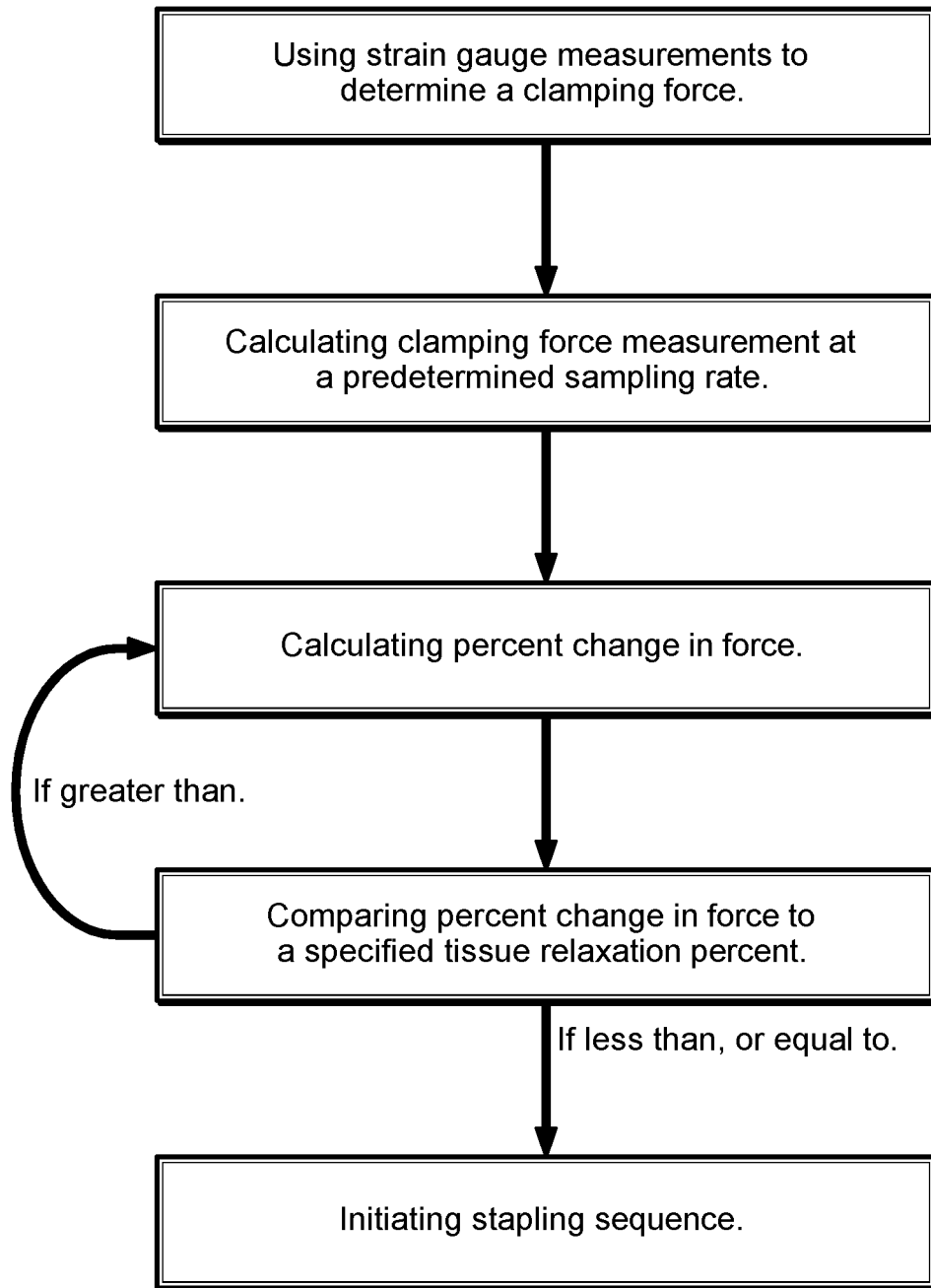
FIG. 6 is a flow diagram of a processing step of the stapling sequence in the flow diagram shown in FIG. 5.

FIG. 6 is a flow diagram detailing the tissue relaxation optimization procedure. Although shown using a 6-tap strain gauge history buffer, which is updated at a specified sampling rate, it is envisioned that more or less than a 6-tap strain gauge history buffer may be utilized. In one aspect of the disclosure, the sampling rate is 400 milliseconds intervals.

After the buffer fills, consecutive strain gauge values are subtracted to calculate the differential change in force and then divided by the previous absolute strain gauge value to determine the percent change in force applied to tissue. This results in five (5) delta percent values which are then averaged. At the next time period, all values in the buffer are shifted down and the new value is placed in the SGFt0 slot. In this manner, only the last five values are used in the calculation. When a new calculation is done, the oldest value is dropped and does not form part of the new calculation. When the averaged delta percent values are less than or equal to a specified tissue relaxation percent, the tissue is determined to be relaxed and the user is encouraged to initiate the firing. As noted above, in certain aspects of the disclosure, at a tissue relaxation percent of between about 0.5% and about 1.0%, tissue is deemed to be sufficiently stabilized, and no further significant change in force is likely.

The 6-tap strain gauge history is SGFt5, SGFt4, SGFt3, SGFt2, SGFt1, SGFt0.

The delta percentages (DP) are calculated as follows:

$$DPt4 = \frac{SGFt5 - SGFt4}{SGFt5}$$

$$DPt3 = \frac{SGFt4 - SGFt3}{SGFt4}$$

$$DPt2 = \frac{SGFt3 - SGFt2}{SGFt3}$$

$$DPt1 = \frac{SGFt2 - SGFt1}{SGFt2}$$

$$DPt0 = \frac{SGFt1 - SGFt0}{SGFt1}$$

The Percent Reduction (PR) is determined by averaging the Delta Percentages as follows:

$$PRt0 = \frac{DPt4 + DPt3 + DPt2 + DPt1 + DPt0}{5}$$

As noted above, if the predetermined tissue relaxation percent is not detected within 15 seconds, the tissue is determined to be relaxed and the user is encouraged to initiate firing.

The above described devices and methods allow clinicians to make a more informed decision about whether clamped tissue has relaxed to a point where the tissue damage is minimized. The software also allows for collection of tissue relaxation data which can be analyzed later to better understand how tissue behaves after clamp and before firing in a real firing.

Persons skilled in the art will understand that the devices and methods specifically described herein and illustrated in the accompanying drawings are non-limiting and exemplary. It is envisioned that the elements and features illustrated or described in connection with one aspect of the disclosure may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

What is claimed is:

1. A circular stapling device comprising:
a handle assembly including a processor;
an adapter assembly operably secured to the handle assembly and including a trocar assembly and a strain gauge assembly;
a reload assembly operably secured to the adapter assembly, the reload assembly including a staple cartridge;
an anvil assembly releasably secured to the trocar assembly and moveably positioned relative to the staple cartridge between a spaced position and a clamped position; and a memory including instructions stored thereon, which when executed by the processor cause the circular stapling device to:
capture a plurality of strain gauge value measurements at a predetermined sampling rate for tissue clamped between the staple cartridge and the anvil assembly;
determine a differential change in force based on subtracting consecutively sampled strain gauge value measurements from each other;
determine a percentage change in force based on dividing the differential change in force by a previous strain gauge measurement value;
determine a percent reduction based on averaging the percent change in force;
determine if the percent reduction is equal to or less than a predetermined threshold value, wherein the predetermined threshold value indicates a tissue relaxation; and
initiating a stapling sequence when the percent reduction is equal to or is less than the predetermined threshold value.

2. The circular stapling device of claim 1, wherein the predetermined threshold value is between about 1% and about 0.5%.

3. The circular stapling device of claim 1, wherein the strain gauge assembly includes a plurality of strain gauges.

4. The circular stapling device of claim 1, wherein the instructions, when executed by the processor, further cause the circular stapling device activate an alert when the predetermined threshold value is achieved.

5. The circular stapling device of claim 4, wherein the instructions, when executed by the processor, further cause the circular stapling device to alert a clinician with an audible, visual, and/or tactile feedback.

6. The circular stapling device of claim 1, wherein the instructions, when executed by the processor, further cause the circular stapling device to initiate a cutting sequence at a completion of the stapling sequence.

7. The circular stapling device of claim 1, wherein the instructions, when executed by the processor, further cause the circular stapling device to activate an alert after the tissue is clamped for a predetermined time period.

8. The circular stapling device of claim 7, wherein the predetermined time is 15 seconds.

9. The circular stapling device of claim 1 wherein the predetermined sampling rate is 400 milliseconds.

10. A method of optimizing tissue relaxation during a stapling procedure, the method comprising:
clamping tissue between an anvil assembly and a reload assembly;
capturing a plurality of strain gauge value measurements at a predetermined sampling rate for tissue clamped between the reload assembly and the anvil assembly;
determining a differential change in force based on subtracting consecutively sampled strain gauge value measurements from each other;
determining a percentage change in force based on dividing the differential change in force by a previous strain gauge measurement value;
determining a percent reduction based on averaging the percent change in force; and
determining if the percent reduction is equal to or less than a predetermined threshold value, wherein the predetermined threshold value indicates a tissue relaxation; and
initiating a stapling sequence when the percent reduction equals or is less than the predetermined threshold value.

11. The method of claim 10, wherein clamping the tissue includes moving the anvil assembly relative to the reload assembly until a predetermined gap is achieved between the anvil assembly and a staple cartridge of the reload assembly.

12. The method of claim 10, wherein calculating the differential change in force includes using a 6-tap strain gauge history buffer.

13. The method of claim 10, wherein initiating the stapling sequence occurs when the percent reduction is between about 0.5% and 1%.

14. The method of claim 10, wherein initiating the stapling sequence occurs 15 seconds after clamping tissue is complete.

15. The method of claim 10, further including initiating a cutting sequence.

16. The method of claim 15, wherein the cutting sequence is initiated at a completion of the stapling sequence.

17. The method of claim 16, wherein the cutting sequence is initiated when the percent reduction equals or is less than a second predetermined threshold value, or after a predetermined time period has elapsed, whichever occurs first.

18. The method of claim 15, wherein initiating the cutting sequence is automatic.

19. The method of claim 10, wherein initiating the stapling sequence occurs when the percent reduction equals or is less than a predetermined threshold value, or after predetermined time elapses, whichever occurs first.

* * * * *